United States Patent
Gebert-Schwarzwaelder et al.

(10) Patent No.: US 11,202,742 B2
(45) Date of Patent: Dec. 21, 2021

(54) PRODUCT FOR LIGHTENING HAIR, CONTAINING SPECIAL OXO-CARBOXYLIC ACIDS

(71) Applicant: Henkel AG & Co. KGaA, Duesseldorf (DE)

(72) Inventors: Antje Gebert-Schwarzwaelder, Neuss (DE); Annika Koenen, Grevenbroich (DE); Astrid Kroos, Monheim (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 16/616,629

(22) PCT Filed: May 24, 2018

(86) PCT No.: PCT/EP2018/063617
§ 371 (c)(1),
(2) Date: Nov. 25, 2019

(87) PCT Pub. No.: WO2019/001856
PCT Pub. Date: Jan. 3, 2019

(65) Prior Publication Data
US 2020/0188246 A1 Jun. 18, 2020

(30) Foreign Application Priority Data
Jun. 27, 2017 (DE) ...................... 10 2017 210 809.6

(51) Int. Cl.
| | | |
|---|---|---|
| *A61Q 5/08* | (2006.01) | |
| *A61K 8/22* | (2006.01) | |
| *A61K 8/23* | (2006.01) | |
| *A61K 8/362* | (2006.01) | |
| *A61K 8/365* | (2006.01) | |
| *A61K 8/41* | (2006.01) | |

(52) U.S. Cl.
CPC .................. *A61K 8/22* (2013.01); *A61K 8/23* (2013.01); *A61K 8/362* (2013.01); *A61K 8/365* (2013.01); *A61K 8/41* (2013.01); *A61Q 5/08* (2013.01); *A61K 2800/88* (2013.01)

(58) Field of Classification Search
None
See application file for complete search history.

(56) References Cited

U.S. PATENT DOCUMENTS

| | | | |
|---|---|---|---|
| 2012/0204357 A1 | 8/2012 | Lalleman et al. | |
| 2017/0340553 A1* | 11/2017 | Anderheggen | A61K 8/86 |
| 2018/0000703 A1 | 1/2018 | Wagner | |
| 2019/0201308 A1* | 7/2019 | Flohr | A61K 8/368 |

FOREIGN PATENT DOCUMENTS

| | | | |
|---|---|---|---|
| DE | 202016008131 U1 | | 4/2017 |
| EP | 2478892 A1 | | 7/2012 |
| EP | 3181113 A1 | | 6/2017 |
| EP | 3287120 A1 | | 2/2018 |
| JP | 2013053113 A | * | 3/2013 |
| JP | 2014080384 A | | 5/2014 |

OTHER PUBLICATIONS

EPO, International Search Report and Written Opinion issued in International Application No. PCT/EP2018/063617, dated Aug. 15, 2018.

* cited by examiner

*Primary Examiner* — Jyothsna A Venkat
(74) *Attorney, Agent, or Firm* — Lorenz & Kopf, LLP

(57) ABSTRACT

A multi-component packaging unit (kit of parts) for lightening keratinous fibres, in particular human hair, which includes, formulated separately from one another,
  a first container containing a cosmetic agent (A), and
  a second container containing a cosmetic agent (B), wherein
  the agent (A) in the first container contains
    (a) at least one peroxy compound, for example hydrogen peroxide, and
  the agent (B) in the second container contains
    (b) at least one acid with formula (I):

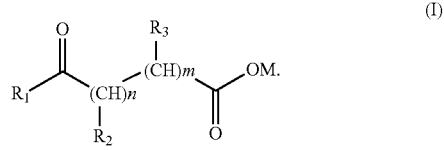

Also, a method for lightening hair, in which the multi-component packaging unit as contemplated herein is used.

3 Claims, No Drawings

PRODUCT FOR LIGHTENING HAIR, CONTAINING SPECIAL OXO-CARBOXYLIC ACIDS

CROSS-REFERENCE TO RELATED APPLICATION

This application is a U.S. National-Stage entry under 35 U.S.C. § 371 based on International Application No. PCT/EP2018/063617, filed May 24, 2018, which was published under PCT Article 21(2) and which claims priority to German Application No. 10 2017 210 809.6, filed Jun. 27, 2017, which are all hereby incorporated in their entirety by reference.

TECHNICAL FIELD

The present disclosure relates to the field of cosmetics. The subject matter of the present disclosure is a multi-component packaging unit for lightening keratinous fibres, in particular human hair, which includes, formulated separately, at least one first agent with a peroxy compound and at least one second agent with a special oxocarboxylic acid.

BACKGROUND

A method for lightening hair in which the said multi-component packaging unit is used constitutes a further aspect of the present disclosure.

During the oxidative colouring or bleaching of hair, a problem concerning damage to the keratinous fibres can occur due to the aggressive agents employed. In particular, the natural hydrophobic nature of the keratinous fibres is reduced, because the colouring or lightening agent initially has to render the hair capable of being penetrated, so that it can take effect. However, the water-repellent nature on the one hand provides the hair with a natural protection, and on the other hand is closely linked to characteristics which are desirable to the consumer, such as shine, smoothness, feel and "flow" of the hair.

In order to overcome the above disadvantages, in the prior art, the use of what are known as keratin cross-linking agents is known. Keratin cross-linking agents are unsaturated, monomeric compounds with a molar mass of less than about 500 g/mol. If the keratin cross-linking agents are then used on hair, then because of their small molecular mass, they can diffuse well into the hair fibres. In the interior of the hair fibre, the keratin cross-linking agents can then form adducts—either directly with the hair fibre or with other cross-linking agent molecules—wherein this adduct formation occurs at the double bond of a respective cross-linking agent molecule.

Relevant keratin cross-linking agents are described in EP 2478892 A1, for example. From a chemical viewpoint, this cross-linking concerns addition to a double bond. In order to activate the double bond of the keratin cross-linking agent, this is frequently found in the direct vicinity of a strongly electron-withdrawing group (such as a carboxy group, for example). In addition, the addition reaction may also be facilitated by using initiators. In EP 2478892 A1, persulphates, peracids or azo compounds, for example, may also be used as initiators. The optimum pH for this reaction described in this connection is an acidic range of from about 4.0 to about 6.9.

During the course of the studies which underlie this application, however, it was discovered that the keratin cross-linking agents described in EP 2478892 A1 were not optimally tailored to bleaching or lightening keratinous fibres.

Employing an alkaline pH is unavoidable when aiming for a sufficiently strong bleaching effect. If the acidic pH proposed in EP 2478892 A1 were to be employed, then the bleaching power would be far too weak.

Thus, the objective of the present disclosure is to provide an agent for the oxidative lightening or bleaching of hair which does not damage the hair, or damages it as little as possible, but nevertheless which has a very strong lightening power.

In this regard, in particular, lightening agents are provided by employing which the hair can be strongly bleached without, however, making the hair brittle, lacking in shine or damaging it in another manner. Despite strong lightening, the entire hair fibre is stabilized. Furthermore, the intended protection of the hair takes as little time as possible, and as far as possible is carried out together with the colouring or lightening step.

It has now been established that the objective defined above can be entirely achieved if a multi-component packaging unit is used for the lightening or bleaching which includes at least two agents (A) and (B) formulated separately in two containers.

Agent (A), which is in the first container, constitutes an oxidizing agent preparation and contains at least one peroxy compound, for example hydrogen peroxide. The second agent (B) contains at least one oxocarboxylic acid with a special formula (I).

BRIEF SUMMARY

In a first aspect, the present disclosure provides a multi-component packaging unit (kit of parts) for lightening keratinous fibres, in particular human hair, which includes, formulated separately from one another, a first container containing a cosmetic agent (A), and
a second container containing a cosmetic agent (B), wherein
the agent (A) in the first container contains
  (a) at least one peroxy compound, for example hydrogen peroxide, and
  the agent (B) in the second container contains
  (b) at least one acid with formula (I):

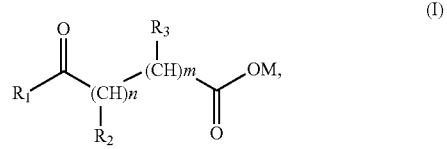

wherein
$R_1$ represents a $C_1$-$C_6$ alkyl group, a $C_2$-$C_6$ alkenyl group, a $C_1$-$C_6$ alkoxy group, a hydroxy group or an aryl group,
$R_2$, $R_3$ independently of each other, represent a hydrogen atom, a $C_1$-$C_6$ alkyl group, a $C_2$-$C_6$ alkenyl group, an aryl group, a hydroxy group or a halogen atom,
M represents a hydrogen atom or one equivalent of a monovalent or multivalent cation,
n represents a whole number from 1 to 4, and
m represents a whole number from 0 to 4.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has been shown that, by using the multi-component packaging unit as contemplated herein, fewer breakages of hair occurred upon subsequent combing and the stability of the fibres was enhanced. The enhancement of the stability of the fibres could be determined, for example, by using DSC (Differential Scanning calorimetry) measurements. Furthermore, the hair lost less elasticity than when bleaching agents which were not as contemplated herein were applied. The elasticity of a hair may, for example, be measured by employing tensile elongation measurements.

The term "lightening keratinous fibres" which is used in the present disclosure should in particular be understood to mean bleaching the fibres or turning them blond. After using the lightening agent, the treated keratinous fibres have a lighter shade than before the lightening or bleaching agent was used. The strength of the lightening may, for example, be assessed visually or in fact be quantified by employing a colorimetric measurement of the strands of hair (measurement of L*a*b* value). In a colorimetric measurement, the L value provides the brightness of a keratinous fibre or strand of hair (L=100 means that the strand of hair is diffusely white; L=0 means that the strand of hair is black). After using the lightening agent as contemplated herein, therefore, the strands have a higher L value.

The term "lightening keratinous fibres" which is used in the present disclosure should also be understood to mean a lightening coloration (or bleaching and colouring). In this case, the agent may also contain dyes in addition to the peroxy compound, wherein, however, the agent only contains these dyes in small quantities in order to provide the lightening result with nuances. After using a dye-containing lightening agent, the treated keratinous fibres thus also have a lighter shade than prior to using the agent.

The agents (A) and (B) as contemplated herein contain the respective components (a) and (b) which are essential to the present disclosure in a cosmetic support. For the purposes of lightening (or lightening colouring), examples of supports of this type are creams, emulsions, gels or surfactant-containing foaming solutions, such as, for example, shampoos, foam aerosols, form formulations or other preparations which are suitable for application to the hair. For example, the cosmetic supports for agent (A) and/or (B) are aqueous or aqueous-alcoholic.

In the context of the present disclosure, the term "aqueous-alcoholic solutions" in particular means aqueous solutions containing from about 0.1% to about 70% by weight of a $C_1$-$C_4$ alcohol, in particular ethanol or isopropanol. The agents as contemplated herein may additionally contain further organic solvents such as, for example, methoxybutanol, benzyl alcohol, ethyl diglycol or 1,2-propylene glycol. In this regard, any water-soluble organic solvents are exemplary.

Agent (A)

The multi-component packaging unit as contemplated herein includes a first container which contains the agent (A). The agent (A) contains at least one peroxy compound as the component (a) which is essential to the present disclosure. The peroxy compound (a) is an oxidizing agent which carries out the lightening or bleaching of the keratinous fibres. More particularly for example, the peroxy compound is hydrogen peroxide.

Hydrogen peroxide is either used in the form of its aqueous solution and/or in the form of one of its solid addition products to organic or inorganic compounds such as urea, melamine and sodium borate. More particularly for example, hydrogen peroxide is used in the form of its aqueous solution.

For example, the quantity of oxidizing agent in the agent (A) as contemplated herein is from about 0.1% to about 12.5% by weight, for example from about 1.5% to about 12.5% by weight, such as from about 4.5% to about 12.5% by weight and such as from about 6.5% to about 12.5% by weight of hydrogen peroxide (calculated as 100% $H_2O_2$), respectively with respect to the total weight of the agent (A).

In a suitable embodiment, a multi-component packaging unit as contemplated herein is exemplified in that the agent (A) in the first container contains—with respect to the total weight of the agent (A)—from about 0.1% to about 12.5% by weight, for example from about 1.5% to about 12.5% by weight, such as from about 4.5% to about 12.5% by weight and such as from about 6.5% to about 12.5% by weight of hydrogen peroxide (a).

Agent (B)

The multi-component packaging unit as contemplated herein furthermore includes a second container, which contains the agent (B) in a cosmetic support. The agent (B) contains at least one acid with formula (I) as the component (b) which is essential to the present disclosure:

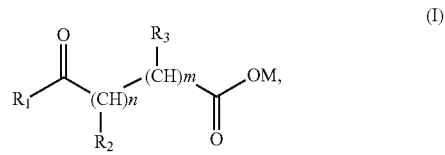

wherein
$R_1$ represents a $C_1$-$C_6$ alkyl group, a $C_2$-$C_6$ alkenyl group, a $C_1$-$C_6$ alkoxy group, a hydroxy group or an aryl group,
$R_2$, $R_3$ independently of each other, represent a hydrogen atom, a $C_1$-$C_6$ alkyl group, a $C_2$-$C_6$ alkenyl group, an aryl group, a hydroxy group or a halogen atom,
M represents a hydrogen atom or one equivalent of a monovalent or multivalent cation,
n represents a whole number from 1 to 4, and
m represents a whole number from 0 to 4.

It has been shown that the acids with formula (I) as contemplated herein effectively diminish the damage to the keratinous fibres when they are applied to the keratinous fibres during or after bleaching.

Measurements in which the effects of the acids with formula (I) as contemplated herein were compared with the effect of other acids which were not as contemplated herein showed that at the same pH, the acids with formula (I) had a greatly improved texturization and an enhanced protection of the keratinous fibres and effectively minimized the damage to the keratinous fibres brought about by the bleaching.

Examples of the substituents $R_1$, $R_2$ and $R_3$ mentioned in formula (I) will now be cited by way of example: examples of $C_1$-$C_6$ alkyl groups are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, —$(CH_2)_5CH_3$. Suitable alkyl residues are methyl and ethyl. Examples of $C_2$-$C_6$ alkenyl groups are vinyl, prop-2-enyl (allyl), 2-methyl-prop-2-enyl, but-3-enyl, but-2-enyl, pent-4-enyl or pent-3-enyl. Examples of a $C_1$-$C_6$ alkoxy group are the methoxy group and the ethoxy group, wherein the methoxy group is suitable. An example of an aryl group is a phenyl group. Examples of halogen atoms are chlorine, bromine, fluorine and iodine, wherein chlorine and bromine are suitable.

In the carboxylic acids with formula (I), the residue $R_1$ represents a $C_1$-$C_6$ alkyl group, a $C_2$-$C_6$ alkenyl group, a $C_1$-$C_6$ alkoxy group, a hydroxy group or an aryl group.

In this connection, it has been shown that with the acids with formula (I), the best protective effect can be obtained when $R_1$ represents a $C_1$-$C_6$ alkyl group, for example a methyl group, an ethyl group or a propyl group, and such as a methyl group.

In a suitable embodiment, a multi-component packaging unit (kit of parts) as contemplated herein is exemplified in that the agent (B) in the second container contains at least one acid with formula (I), wherein
$R_1$ represents a $C_1$-$C_6$ alkyl group, for example a methyl group, an ethyl group or a propyl group, and in an embodiment a methyl group.

In the carboxylic acids with formula (I), the residues $R_2$ and $R_3$ may be selected independently of each other. The residues $R_2$, $R_3$, independently of each other, represent a hydrogen atom, a $C_1$-$C_6$ alkyl group, a $C_2$-$C_6$ alkenyl group, an aryl group, a hydroxy group or a halogen atom.

It has also been shown that the carboxylic acids with formula (I) are particularly well suited to accomplishing the task set by the present disclosure when the residues $R_2$ and $R_3$, independently of each other, represent a hydrogen atom, a $C_1$-$C_6$ alkyl group or a $C_2$-$C_6$ alkenyl group.

In a suitable embodiment, a multi-component packaging unit (kit of parts) as contemplated herein is exemplified in that the agent (B) in the second container contains at least one acid with formula (I), wherein
$R_2$, $R_3$ independently of each other, represent a hydrogen atom, a $C_1$-$C_6$ alkyl group or a $C_2$-$C_6$ alkenyl group.

In a further suitable embodiment, a multi-component packaging unit (kit of parts) as contemplated herein is exemplified in that the agent (B) in the second container contains at least one acid with formula (I), wherein
$R_2$, $R_3$ both represent a hydrogen atom.

Thus, a more suitable multi-component packaging unit (kit of parts) for lightening keratinous fibres, in particular human hair, includes, formulated separately from one another,
a first container containing a cosmetic agent (A), and
a second container containing a cosmetic agent (B), wherein
the agent (A) in the first container contains (a) hydrogen peroxide, and
the agent (B) in the second container contains
(b) at least one acid with formula (I):

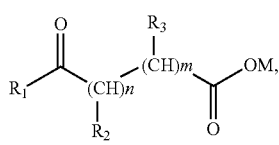
(I)

wherein
$R_1$ represents a $C_1$-$C_6$ alkyl group,
$R_2$, $R_3$ independently of each other, represent a hydrogen atom, a $C_1$-$C_6$ alkyl group or a $C_2$-$C_6$ alkenyl group,
M represents a hydrogen atom or one equivalent of a monovalent or multivalent cation,
n represents a whole number from 1 to 4, and
m represents a whole number from 0 to 4.

Thus, a more suitable multi-component packaging unit (kit of parts) for lightening keratinous fibres, in particular human hair, includes, formulated separately from one another,
a first container containing a cosmetic agent (A), and
a second container containing a cosmetic agent (B), wherein
the agent (A) in the first container contains (a) hydrogen peroxide, and
the agent (B) in the second container contains
(b) at least one acid with formula (I):

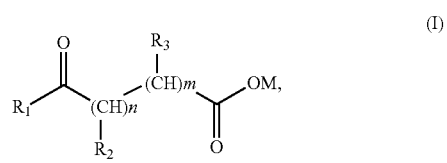
(I)

wherein
$R_1$ represents a $C_1$-$C_6$ alkyl group,
$R_2$, $R_3$ both represent a hydrogen atom,
M represents a hydrogen atom or one equivalent of a monovalent or multivalent cation,
n represents a whole number from 1 to 4, and
m represents a whole number from 0 to 4.

In the compounds with formula (I), n gives the number of repeat units for the group ($CHR_2$). In analogous manner, m gives the number of repeat units for the group ($CHR_3$).

If, for example, n represents the number 1, and m represents the number 1, then the acid with formula (I) is the compound $R_1C(O)$—$CHR_2$—$CHR_3$—COOM.
If, for example, n represents the number 2, and m represents the number 1, then the acid with formula (I) is the compound $R_1C(O)$—$CHR_2$—$CHR_2$—$CHR_3$—COOM.
If, for example, n represents the number 1, and m represents the number 2, then the acid with formula (I) is the compound $R_1C(O)$—$CHR_2$—$CHR_3$—$CHR_3$—COOM.

In a suitable embodiment, a multi-component packaging unit (kit of parts) as contemplated herein is exemplified in that the agent (B) in the second container contains at least one acid with formula (I), wherein
n represents the number 1 or 2, and
m represents the number 0 or 1.

Thus, a more suitable multi-component packaging unit (kit of parts) for lightening keratinous fibres, in particular human hair, includes, formulated separately from one another,
a first container containing a cosmetic agent (A), and
a second container containing a cosmetic agent (B), wherein
the agent (A) in the first container contains (a) hydrogen peroxide, and
the agent (B) in the second container contains
(b) at least one acid with formula (I):

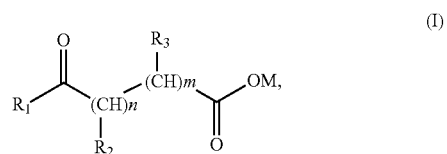
(I)

wherein $R_1$ represents a $C_1$-$C_6$ alkyl group, $R_2$, $R_3$ independently of each other, represent a hydrogen atom, a $C_1$-$C_6$ alkyl group or a $C_2$-$C_6$ alkenyl group, M represents a hydrogen atom or one equivalent of a monovalent or multivalent cation, n represents the number 1 or 2, and m represents the number 0 or 1.

It has been shown to be more particularly preferable for m to represent the number 0. In the context of this suitable embodiment, the acid with formula (I) is a compound with formula (Ia):

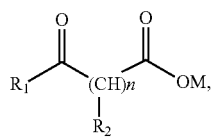

(Ia)

wherein $R_1$ represents a $C_1$-$C_6$ alkyl group, a $C_2$-$C_6$ alkenyl group, a $C_1$-$C_6$ alkoxy group, a hydroxy group or an aryl group, $R_2$ represents a hydrogen atom, a $C_1$-$C_6$ alkyl group or a $C_2$-$C_6$ alkenyl group, M represents a hydrogen atom or one equivalent of a monovalent or multivalent cation, and n represents a whole number from 1 to 4.

Thus, a more suitable multi-component packaging unit (kit of parts) for lightening keratinous fibres, in particular human hair, includes, formulated separately from one another, a first container containing a cosmetic agent (A), and a second container containing a cosmetic agent (B), wherein the agent (A) in the first container contains (a) hydrogen peroxide, and the agent (B) in the second container contains (b) at least one acid with formula (Ia):

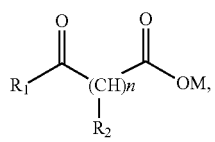

(Ia)

wherein $R_1$ represents a $C_1$-$C_6$ alkyl group, $R_2$ represents a hydrogen atom, a $C_1$-$C_6$ alkyl group, a $C_2$-$C_6$ alkenyl group, an aryl group, a hydroxy group or a halogen atom, M represents a hydrogen atom or one equivalent of a monovalent or multivalent cation, and n represents a whole number from 1 to 4.

It has been shown to be even more particularly preferable for n to represent the number 2.

In the context of this more suitable embodiment, the acid with formula (I) is a compound with formula (Ia)

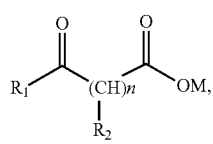

(Ia)

wherein $R_1$ represents a $C_1$-$C_6$ alkyl group, $R_2$ represents a hydrogen atom, a $C_1$-$C_6$ alkyl group, a $C_2$-$C_6$ alkenyl group, an aryl group, a hydroxy group or a halogen atom, M represents a hydrogen atom or one equivalent of a monovalent or multivalent cation, and n represents the number 1 or 2.

Thus, a more suitable multi-component packaging unit (kit of parts) for lightening keratinous fibres, in particular human hair, includes, formulated separately from one another, a first container containing a cosmetic agent (A), and a second container containing a cosmetic agent (B), wherein the agent (A) in the first container contains (a) hydrogen peroxide, and the agent (B) in the second container contains (b) at least one acid with formula (Ia):

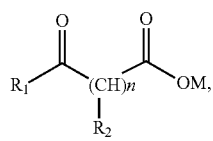

(Ia)

wherein $R_1$ represents a $C_1$-$C_6$ alkyl group, $R_2$ represents a hydrogen atom or a $C_1$-$C_6$ alkyl group, M represents a hydrogen atom or one equivalent of a monovalent or multivalent cation, and n represents the number 2.

In the compounds with formula (I) (or (Ia)), M represents a hydrogen atom or one equivalent of a monovalent or multivalent cation.

When M represents a hydrogen atom, then the compound with formula (I) is in the form of its acid. The hydrogen atom of the acid function is acidic, and the acid deprotonates in an aqueous medium. For this reason, the acid (I) (or (Ia)) in the cosmetic agent (B)—in particular when this includes an aqueous cosmetic support—is present in equilibrium with its anion.

The acid may also be used directly in the form of its salt in the cosmetic agent (B). In this case, the carboxylate anion is neutralized by M, wherein M represents one equivalent of a monovalent or multivalent cation. Particularly suitable inorganic cations which may be mentioned are $Na^+$, $K^+$, $(NH_4)^+$, ½ $Mg^{2+}$, ½ $Ca^{2+}$. Organic cations such as tetra-$C_1$-$C_{22}$ alkylammonium are also suitable.

More particularly for example having regard to the solution of the task set by the present disclosure, the agent (B) contains water and the pH is set up to be acidic. The acidic pH may, for example, be set up by using the acid(s) with formula (I) (or (Ia)) in the form of their free acids. For this reason, it has been shown to be more particularly preferable for M to represent a hydrogen atom.

In a suitable embodiment, a multi-component packaging unit (kit of parts) is exemplified in that the agent (B) in the second container contains at least one acid with formula (I) (or (Ia)), wherein
M represents a hydrogen atom.

Exemplary agents (B) as contemplated herein for lightening keratinous fibres contain at least one carboxylic acid with formula (I) which is selected from

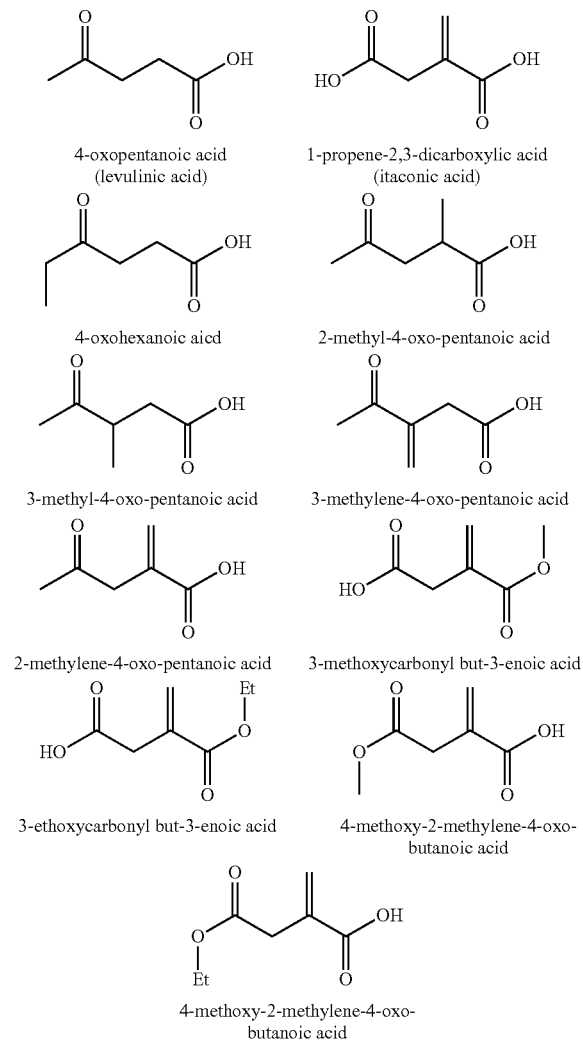

4-oxopentanoic acid (levulinic acid)

1-propene-2,3-dicarboxylic acid (itaconic acid)

4-oxohexanoic aicd 2-methyl-4-oxo-pentanoic acid 3-methyl-4-oxo-pentanoic acid 3-methylene-4-oxo-pentanoic acid 2-methylene-4-oxo-pentanoic acid 3-methoxycarbonyl but-3-enoic acid 3-ethoxycarbonyl but-3-enoic acid 4-methoxy-2-methylene-4-oxo-butanoic acid 4-methoxy-2-methylene-4-oxo-butanoic acid More explicitly more suitable compounds within the group of exemplary carboxylic acids with formula (I) mentioned above are those selected from:
4-oxopentanoic acid (levulinic acid) and
1-propene-2,3-dicarboxylic acid (itaconic acid).
4-oxopentanoic acid (levulinic acid) and 1-propene-2,3-dicarboxylic acid (itaconic acid) are commercially available.

In order to obtain an optimized protection of the fibres, the agents (B) as contemplated herein for example contain the acid or acids with formula (I) in specific ranges of quantities. More particularly for example, the agent (B) as contemplated herein—with respect to its total weight—contains (b) one or more acids with formula (I) in a total quantity of from about 0.1% to about 10.0% by weight, for example of from about 0.3% to about 8.5% by weight, such as of from about 0.5% to about 7.5% by weight and such as of from about 0.7% to about 6.5% by weight.

In a suitable embodiment, a multi-component packaging unit (kit of parts) is exemplified in that the agent (B) in the second container contains—with respect to the total weight of the agent (B)—one or more acids with formula (I) in a total quantity of from about 0.1% to about 10.0% by weight, for example of from about 0.3% to about 8.5% by weight, such as of from about 0.5% to about 7.5% by weight and such as of from about 0.7% to about 6.5% by weight.

pH Pf the Agent (B)

As already described above, more suitable acids with formula (I) in the agent (B) as contemplated herein which are used are those in which M represents a hydrogen atom, i.e. the use of acids in their free form has been shown to be particularly suitable. In this manner, the acidity of the acid group contributes to ensuring that the pH of the agent (B) is in the acidic range. In an embodiment, the agent (B) contains water.

Having regard to the solution of the present disclosure to the set task, it has been shown to be particularly suitable to set the pH of the agent (B) to a value in the range from about 1.0 to about 4.5, for example from about 1.2 to about 4.0, such as from about 1.5 to about 3.5 and such as from about 1.8 to about 3.0.

In a suitable embodiment, a multi-component packaging unit (kit of parts) is exemplified in that the agent (B) in the second container contains water and has a pH of from about 1.0 to about 4.5, for example of from about 1.2 to about 4.0, such as of from about 1.5 to about 3.5 and such as of from about 1.8 to about 3.0.

The pH may, for example, be measured using a glass electrode which is usually commercially available in the form of a combination electrode. Prior to measuring the pH, the glass electrode is usually calibrated using calibration solutions with known pHs. The term "pH" as used in the context of the present disclosure should be understood to mean values for the pH which are measured at a temperature of about 22° C.

In order to set the exemplary pH, in particular, the acids with formula (I) may be used. In addition, other quantities of acidification agents may be contained in agent (B). Examples of further acidification agents which are suitable in the context of the present disclosure are citric acid, lactic acid, acetic acid, tartaric acid, malic acid, etidronic acid, pyridine-2,6-dicarboxylic acid or even dilute mineral acids (such as hydrochloric acid, sulphuric acid, phosphoric acid).

For the fine adjustment of the pH, moreover, various alkalizing agents may be used in agent (B). Suitable alkalizing agents in the context of the present disclosure may be selected from the group which is formed by ammonia, alkanolamines, alkali metal hydroxides, alkali metal metasilicates, alkali metal phosphates and alkali metal hydrogen phosphates. Exemplary inorganic alkalizing agents are sodium hydroxide, potassium hydroxide, sodium silicate and sodium metasilicate. Organic alkalizing agents which may be used as contemplated herein are for example selected from monoethanolamine, 2-amino-2-methylpropanol and triethanolamine. Sodium silicate and sodium metasilicate are more suitable.

Agent (C) in the Third Container

The agents (B) which contain the acids with formula (I) as contemplated herein are extremely suitable for reducing damage which is brought about by bleaching hair and turning it blonde. The hair in this regard is turned blonde by the agent (A) which contains at least one peroxide, for example hydrogen peroxide.

If the consumer wants to have a particularly strong lightening power, then hydrogen peroxide alone as the oxidizing agent is usually not sufficient. In this case, bleaching agents are usually employed which contain a combination of the oxidizing agents hydrogen peroxide and persulphates.

During the course of the studies leading up to this present disclosure, it was established that the agents (B) with the acids with formula (I) also bring about a significance reduction in damage during or in particular after using the hydrogen peroxide/persulphate combination.

For this reason, in an embodiment, the agent (B) with the acids with formula (I) is used after bleaching in which the hair is bleached by employing a combination of hydrogen peroxide and persulphates. To this end, the multi-component packaging unit as contemplated herein for example contains a third separately formulated container which contains a third agent (C). In this regard, this third agent (C) contains ammonium persulphate, potassium persulphate and/or sodium persulphate.

Therefore, a multi-component packaging unit (kit of parts) as contemplated herein which is more suitable includes, formulated separately from one another,
a third container containing a cosmetic agent (C), wherein the agent (C) in the third container contains
(c) at least one persulphate from the group formed by ammonium persulphate, potassium persulphate and/or sodium persulphate.

Persulphates are alternatively also known as peroxodisulphates. Suitable persulphates are ammonium persulphate (ammonium peroxodisulphate), potassium persulphate (potassium peroxodisulphate) and sodium persulphate (sodium peroxodisulphate).

Potassium peroxodisulphate is alternatively also known as potassium persulphate and has the empirical formula $K_2S_2O_8$.

Ammonium peroxodisulphate is alternatively also known as ammonium persulphate and has the empirical formula $(NH_4)_2S_2O_8$.

Sodium peroxodisulphate is alternatively also known as sodium persulphate and has the empirical formula $Na_2S_2O_8$.

The persulphate or persulphates are for example employed in agent (C) in a total quantity of from about 1.0% to about 40.0% by weight, for example of from about 5.0% to about 30.0% by weight, such as of from about 10.0% to about 25% by weight and more particularly from about 15.0% to about 20.0% by weight, wherein the said quantities are given with respect to the total quantity of the persulphates employed in the agent (C) which is in relation to the total weight of the agent (C).

Thus, a more suitable multi-component packaging unit (kit of parts) for lightening keratinous fibres, in particular human hair, includes, formulated separately from one another,
a first container containing a cosmetic agent (A), and
a second container containing a cosmetic agent (B), and
a third container containing a cosmetic agent (C), wherein
the agent (A) in the first container contains (a) hydrogen peroxide, and
the agent (B) in the second container contains
(b) at least one acid with formula (I):

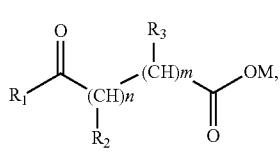

wherein
$R_1$ represents a $C_1$-$C_6$ alkyl group, a $C_2$-$C_6$ alkenyl group, a $C_1$-$C_6$ alkoxy group, a hydroxy group or an aryl group,
$R_2$, $R_3$ independently of each other, represent a hydrogen atom, a $C_1$-$C_6$ alkyl group, a $C_2$-$C_6$ alkenyl group, an aryl group, a hydroxy group or a halogen atom,
M represents a hydrogen atom or one equivalent of a monovalent or multivalent cation,
n represents a whole number from 1 to 4, and
m represents a whole number from 0 to 4,
the agent (C) in the third container contains
(c) at least one persulphate from the group formed by ammonium persulphate, potassium persulphate and/or sodium persulphate.

In addition, therefore, a more suitable multi-component packaging unit (kit of parts) for lightening keratinous fibres, in particular human hair, includes, formulated separately from one another,
a first container containing a cosmetic agent (A), and
a second container containing a cosmetic agent (B), and
a third container containing a cosmetic agent (C), wherein
the agent (A) in the first container contains (a) hydrogen peroxide, and
the agent (B) in the second container contains at least one acid with formula (I), which is selected from the group formed by 4-oxopentanoic acid (levulinic acid), 1-propene-2,3-dicarboxylic acid (itaconic acid), 4-oxo-hexanoic acid, 2-methyl-4-oxo-pentanoic acid, 3-methyl-4-oxo-pentanoic acid, 3-methylene-4-oxo-pentanoic acid, 2-methylene-4-oxo-pentanoic acid, 3-methoxycarbonyl but-3-enoic acid, 3-ethoxycarbonyl but-3-enoic acid, 4-methoxy-2-methylene-4-oxo-butanoic acid and 4-methoxy-2-methylene-4-oxo-butanoic acid and
the agent (C) in the third container contains
(c) at least one persulphate from the group formed by ammonium persulphate, potassium persulphate and/or sodium persulphate.

pH of Bleaching Agent

Bleaching of hair or turning it blond usually takes place under alkaline conditions. The alkalizing agent ensures that the hair swells sufficiently; in addition, the bleaching power of hydrogen peroxide or hydrogen peroxide/persulphate is enhanced in an alkaline medium. For this reason, the pH range for ready-to-use bleaching agents is usually from about 7.5 to about 12.5, for example from about 8.5 to about 10.5.

For reasons of stability, the agent (A), which contains hydrogen peroxide, is rendered acidic. For this reason, an alkalizing agent is therefore usually not formulated together with the hydrogen peroxide.

In order to produce an alkaline bleaching agent, the alkalizing agent may therefore be incorporated into the agent (C). The agent (C) contains persulphates and is for example provided in the form of a powder or a paste.

The use of alkalizing agents in agent (C) is therefore particularly suitable for the alkalizing agents which are also in the solid or powdered form. Examples of suitable solid alkalizing agents are alkali metal hydroxides, alkali metal metasilicates, alkali metal phosphates and alkali metal hydrogen phosphates. Exemplary inorganic alkalizing agents are sodium hydroxide, potassium hydroxide, sodium silicate and sodium metasilicate. Sodium silicate and sodium metasilicate are more suitable.

The term "sodium silicates" should be understood to mean the sodium salts of various silicic acids. A distinction may be made between sodium silicates in which the ratio of silicon dioxide to sodium monoxide is greater than or equal to about 2 or less than or equal to about 1. Sodium metasilicate belongs to the latter group, i.e. "sodium metasilicate" should be understood to mean polymeric silicates with formula $[Na_2SiO_3]_x$. Sodium metasilicate may be anhydrous or also in the form of its hydrates.

Furthermore, the sodium silicate may also be used in the form of sodium water glass. The term "sodium water glass" means an amorphous sodium silicate which has solidified from a melt.

In the context of this embodiment, therefore, a exemplary multi-component packaging unit (kit of parts) includes, formulated separately from one another, a third container containing a cosmetic agent (C), wherein the agent (C) in the third container contains (c1) at least one persulphate from the group formed by ammonium persulphate, potassium persulphate and/or sodium persulphate, and (c2) at least one alkalizing agent from the group formed by alkali metal hydroxides, alkali metal metasilicates, alkali metal phosphates and alkali metal hydrogen phosphates.

Exemplary inorganic alkalizing agents are sodium hydroxide, potassium hydroxide, sodium silicate and sodium metasilicate.

On the other hand, the bleaching agent may also be adjusted to the optimized pH by using liquid or free-flowing alkalizing agents. Suitable liquid or free-flowing alkalizing agents which may be cited are ammonia, 2-aminoethan-1-ol, 2-amino-2-methylpropan-1-ol, 2-amino-2-methyl-propan-1,3-diol.

Amino acids such as L-arginine, D-arginine, D/L-arginine, L-lysine, D-lysine and D/L-lysine are also suitable as alkalizing agents.

The alkalizing agents mentioned above may be provided in a further container which contains a further agent (D). In the context of this embodiment, the agent (D) contains at least one alkalizing agent from the group formed by ammonia, 2-aminoethan-1-ol, 2-amino-2-methylpropan-1-ol, 2-amino-2-methyl-propan-1,3-diol, L-arginine, D-arginine, D/L-arginine, L-lysine, D-lysine and D/L-lysine.

Thus, a more suitable multi-component packaging unit (kit of parts) as contemplated herein includes, formulated separately from one another, a further container containing a cosmetic agent (D), wherein the agent (D) in this further container contains (d) at least one alkalizing agent from the group formed by ammonia, 2-aminoethan-1-ol, 2-amino-2-methylpropan-1-ol, 2-amino-2-methyl-propan-1,3-diol, L-arginine, D-arginine, D/L-arginine, L-lysine, D-lysine and D/L-lysine.

In this context, the multi-component packaging unit as contemplated herein may comprise the agents (A), (B), (C) and (D), but also the agents (A), (B) and (D).

A more suitable multi-component packaging unit (kit of parts) for lightening keratinous fibres, in particular human hair, also includes, formulated separately from one another, a first container containing a cosmetic agent (A), and
a second container containing a cosmetic agent (B), and
a third container containing a cosmetic agent (C), and
a fourth container containing a cosmetic agent (D), wherein the agent (A) in the first container contains (a) hydrogen peroxide, and the agent (B) in the second container contains at least one acid with formula (I), which is selected from the group formed by 4-oxopentanoic acid (levulinic acid), 1-propene-2,3-dicarboxylic acid (itaconic acid), 4-oxohexanoic acid, 2-methyl-4-oxo-pentanoic acid, 3-methyl-4-oxo-pentanoic acid, 3-methylene-4-oxo-pentanoic acid, 2-methylene-4-oxo-pentanoic acid, 3-methoxycarbonyl but-3-enoic acid, 3-ethoxycarbonyl but-3-enoic acid, 4-methoxy-2-methylene-4-oxo-butanoic acid and 4-methoxy-2-methylene-4-oxo-butanoic acid, and the agent (C) in the third container contains (c) at least one persulphate from the group formed by ammonium persulphate, potassium persulphate and/or sodium persulphate, and the agent (D) in the fourth container (d) contains at least one alkalizing agent from the group formed by ammonia, 2-aminoethan-1-ol, 2-amino-2-methylpropan-1-ol, 2-amino-2-methyl-propan-1,3-diol, L-arginine, D-arginine, D/L-arginine, L-lysine, D-lysine and D/L-lysine.

A more suitable multi-component packaging unit (kit of parts) for lightening keratinous fibres, in particular human hair, also, however, includes, formulated separately from one another, a first container containing a cosmetic agent (A), and
a second container containing a cosmetic agent (B), and
a third container containing a cosmetic agent (D), wherein the agent (A) in the first container contains (a) hydrogen peroxide, and the agent (B) in the second container contains at least one acid with formula (I), which is selected from the group formed by 4-oxopentanoic acid (levulinic acid), 1-propene-2,3-dicarboxylic acid (itaconic acid), 4-oxohexanoic acid, 2-methyl-4-oxo-pentanoic acid, 3-methyl-4-oxo-pentanoic acid, 3-methylene-4-oxo-pentanoic acid, 2-methylene-4-oxo-pentanoic acid, 3-methoxycarbonyl but-3-enoic acid, 3-ethoxycarbonyl but-3-enoic acid, 4-methoxy-2-methylene-4-oxo-butanoic acid and 4-methoxy-2-methylene-4-oxo-butanoic acid and the agent (D) in the third container (d) contains at least one alkalizing agent from the group formed by ammonia, 2-aminoethan-1-ol, 2-amino-2-methylpropan-1-ol, 2-amino-2-methyl-propan-1,3-diol, L-arginine, D-arginine, D/L-arginine, L-lysine, D-lysine and D/L-lysine.

Further Ingredients

The agents (A) and (B) (as well as the optional agents (C) and/or (D)) of the multi-component packaging unit as contemplated herein may additionally contain other active substances, auxiliary substances and additives such as, for example, cationic surfactants, non-ionic surfactants, amphoteric or zwitterionic surfactants, anionic surfactants, anionic, non-ionic and/or cationic polymers, structuring agents such as glucose, fragrancing oils, substances that improve the structure of fibres, in particular mono-, di- and oligosaccharides such as, for example, glucose, galactose, fructose, fruit sugar and lactose; colorants to colour the agent; antidandruff substances such as piroctone olamine, zinc omadine and climbazole; amino acids and oligopeptides; animal and/or plant-based protein hydrolysates, as well as in the form of their fatty acid condensation products or optionally anionically or cationically modified derivatives; plant oils; light stabilizers and UV blockers; active substances such as panthenol, pantothenic acid, pantolactone, allantoin, pyrrolidinone carboxylic acids and their salts as well as their colour-changing salts, as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; vitamins, provitamins and vitamin precursors; plant extracts; swelling and penetrating agents such as glycerin, propylene glycol monoethyl ether, carbonates, hydrogen carbonates, guanidines, ureas as well as primary, secondary and tertiary phosphates; opacifiers such as latex, styrene/PVP and styrene/acrylamide copolymers; pearlescent agents such as ethylene glycol monostearate and distearate, as well as PEG-3-distearate; pigments, as well as propellants such as propane-butane mixtures, $N_2O$, dimethyl ether, $CO_2$ and air.

The additional active substances and auxiliary substances are for example used in the agents as contemplated herein in respective quantities of from about 0.0001% to about 10% by weight, in particular from about 0.0005% to about 5% by weight, with respect to the total weight of the respective agent.

Method for Bleaching Hair

The multi-component packaging units described above are used in a method for bleaching or lightening hair.

Thus, in a second aspect, the present disclosure provides a method for lightening hair, comprising the following steps in the specified order:
(1) mixing an agent (A) with an agent (C) and/or with an agent (D), wherein
 the agent (A) is an agent as disclosed in detail in the description of the first aspect of the present disclosure, and
 the agent (C) is an agent as disclosed in detail in the description of the first aspect of the present disclosure, and
 the agent (D) is an agent as disclosed in detail in the description of the first aspect of the present disclosure,
(2) applying the mixture produced in step (1) to the hair,
(3) allowing the mixture applied to the hair in step (2) to take effect,
(4) optionally, rinsing the hair,
(5) applying an agent (B) to the hair, wherein the agent (B) is an agent as disclosed in detail in the description of the first aspect of the present disclosure.

The agent (A) contains hydrogen peroxide and constitutes the oxidizing agent component. In order to produce the ready-to-use bleaching agent, the agent (A)—depending on the desired degree of lightening—is mixed either with agent (C) and/or with agent (D), wherein the agent (C) contains one or more persulphates and the agent (D) contains one or more alkalizing agents (step (1)).

The mixture of the agents (A) and (C) constitutes a ready-to-use bleaching agent. The mixture of the agents (A) and (D) also constitutes a ready-to-use bleaching agent. In addition, the mixture of the agents (A), (C) and (D) constitutes a ready-to-use bleaching agent.

Thus, for example:
 about 100 g of agent (A) can be mixed with about 100 g of agent (C), or indeed
 about 100 g of agent (A) can be mixed with about 100 g of agent (D), or indeed
 about 100 g of agent (A) can be mixed with about 100 g of agent (C) and with about 100 g of agent (D), or indeed
 about 100 g of agent (A) can be mixed with about 50 g of agent (C) and with about 50 g of agent (D).

Other mixing ratios are also as contemplated herein and possible. Thus, agents (A) and (C) can be mixed together in a mixing ratio of from about 1:5 to about 5:1, for example from about 1:3 to about 1:3.

The agents (A) and (D) may, for example, be mixed together in a mixing ratio of from about 1:5 to about 5:1, for example from about 1:3 to about 1:3.

This mixture produced in step (1), which is the ready-to-use bleaching agent, is then applied to the hair (step 2). The application in this regard may be carried out using a gloved hand or with the aid of an applicator (comb, brush or applicette). After application, the ready-to-use bleaching agent is allowed to take effect on the hair, for example for a period of from about 5 to about 60 minutes, for example from about 15 to about 45 minutes (step 3).

Next, the bleaching agent can be rinsed out of the hair (step 4).

It has been shown, and is particularly preferable, that the hair should be rinsed for a short period of from about 5 to about 60 seconds, for example from about 5 to about 45 seconds.

In an embodiment, the method for lightening hair includes the following steps in the specified order:
(1) mixing an agent (A) with an agent (C) and/or with an agent (D), wherein
 the agent (A) is an agent as disclosed in detail in the description of the first aspect of the present disclosure, and
 the agent (C) is an agent as disclosed in detail in the description of the first aspect of the present disclosure, and
 the agent (D) is an agent as disclosed in detail in the description of the first aspect of the present disclosure,
(2) applying the mixture produced in step (1) to the hair,
(3) allowing the mixture applied to the hair in step (2) to take effect,
(4) rinsing the hair for a period of from about 5 to about 60, for example of from about 5 to about 45 seconds,
(5) applying an agent (B) to the hair, wherein the agent (B) is an agent as disclosed in detail in the description of the first aspect of the present disclosure.

In the context of a further embodiment, however, the agent (B) may also be applied to the hair which still has bleaching agent which has been applied to it, without rinsing.

A method for lightening hair comprising the following steps in the specified order is also suitable:
(1) mixing an agent (A) with an agent (C) and/or with an agent (D), wherein
 the agent (A) is an agent as disclosed in detail in the description of the first aspect of the present disclosure, and
 the agent (C) is an agent as disclosed in detail in the description of the first aspect of the present disclosure, and
 the agent (D) is an agent as disclosed in detail in the description of the first aspect of the present disclosure,
(2) applying the mixture produced in step (1) to the hair,
(3) allowing the mixture applied to the hair in step (2) to take effect,
(4) applying an agent (B) to the hair, wherein the agent (B) is an agent as disclosed in detail in the description of the first aspect of the present disclosure.

The agent (B) which contains the acid(s) with formula (I) is applied as a post-treatment agent in the method as contemplated herein; it is applied after applying the ready-to-use bleaching agent to the hair.

In an embodiment, the agent (B) is an aqueous cosmetic agent which has an acidic pH and, for example, may be formulated as a gel, shampoo, conditioner or as a cream.

The statements provided regarding the multi-component packaging unit as contemplated herein are also applicable mutatis mutandis to the further exemplary embodiments of the method of the present disclosure.

EXAMPLES

1. Formulations

The following formulations were produced (all data as a % by weight)

Formulation with Hydrogen Peroxide (Agent (A))

| Substance (INCI) | OX |
| --- | --- |
| Na benzoate | 0.04 |
| Dipicolinic acid | 0.10 |
| Disodium pyrophosphate | 0.10 |
| Potassium hydroxide 50% | 0.19 |
| Propanediol-1,2 | 0.50 |
| HEDP 60% | 0.25 |
| Paraffinum Liquidum | 2.00 |
| Cetearyl Alcohol | 3.60 |
| Ceteareth-20 | 1.20 |
| Hydrogen peroxide 50% | 12.20 |
| Water, demineralized | ad 100 |

Paste with Persulphate (Agent (C))

| Substance (INCI) | V1 |
| --- | --- |
| Versagel M1600 | 5.00 |
| Lanette N | 7.00 |
| Eumulgin B 5 | 4.00 |
| Xanthan NaTrue | 1.50 |
| Sodium metasilicate (anhydrous) | 6.50 |
| Potassium persulphate | 42.00 |
| Fragrance | 0.60 |
| Paraffinum Liquidum | ad 100 |

Versagel M1600: Paraffinum Liquidum (Mineral Oil), Ethylene/Propylene/Styrene Copolymer, Butylene/Ethylene/Styrene Copolymer Lanette N: Cetearyl Alcohol, Sodium Cetearyl Sulfate Eumulgin B 5: Ceteareth-50

Xanthan NaTrue: Xanthan Gum

Post-Treatment Agent (B)

|  | (B1) E | (B2) V | (B3) E | (B4) V | (B5) E | (B6) V |
| --- | --- | --- | --- | --- | --- | --- |
| Levulinic acid | 1.0 | — | 5.0 | — | 10.0 | — |
| Hydrochloric acid | — | ad pH 2.7 | — | ad pH 2.3 | — | ad pH 2.2 |
| pH | 2.7 | 2.7 | 2.3 | 2.3 | 2.2 | 2.2 |
| Water | ad 100 | ad 100 | ad 100 | ad 100 | ad 100 | ad 100 |

Levulinic Acid (Alternative Name: 4-oxo-pentanoic acid, CAS No. 123-76-2, Merck)

|  | (B7) E | (B8) V | (B9) E | (B10) V | (B11) E | (B12) V |
| --- | --- | --- | --- | --- | --- | --- |
| Levulinic acid | 3.0 | — | — | — | — | — |
| Itaconic acid | — | — | 0.14 | — | 0.56 | — |
| Hydrochloric acid | — | ad 2.4 | — | ad pH 2.7 | — | ad pH 2.3 |
| pH | 2.4 | 2.4 | 2.7 | 2.7 | 2.3 | 2.3 |
| Water | ad 100 | ad 100 | ad 100 | ad 100 | ad 100 | ad 100 |

Itaconic Acid (Alternative Name: methylene succinic acid, 1-propene-2,3-dicarboxylic acid, CAS No. 97-65-4, Merck)

The control (V) in each case was a post-treatment agent which contained no acid with formula (I) as contemplated herein, but to which enough hydrochloric acid had been added to provide the control formulation with the same pH as the corresponding post-treatment agent (E) as contemplated herein.

2. Use

The hydrogen peroxide formulation (agent A) and the persulphate paste (agent C) were each mixed in a ratio of 1:1 and was applied to 12 strands of hair respectively immediately after mixing (treatment time 45 min at room temperature). The pH of the ready-to-use mixture was 9.5 in each case. The strands were rinsed with tap water for 10 seconds upon completion of the treatment time.

The strands acting as the reference (R) were not post-treated with an agent (B), but instead were thoroughly washed with tap water. Next, the strands were immersed in each of the agents (B), respectively for 10 minutes, and after this were rinsed thoroughly with water and dried.

3. Measurement of Fibre Stabilization

The melting points below were determined using DSC analysis (Perkin Elmer DSC-7). A full description of the methods can be found in DE 196 173 95 A1, for example. The higher the measured value (Peak Apex Temp, °C.), the more stable is the keratin matrix of the hair.

Hair Stability (12-Fold Determination with Averaging)

|  | (R) without post-treatment | (B1) E | (B2) V | (B3) E | (B4) V | (B5) E | (B6) V |
| --- | --- | --- | --- | --- | --- | --- | --- |
| DSC: Peak Apex Temp. (° C.) | 143 | 159 | 147 | 163 | 151 | 164 | 157 |

|  | (R) without post-treatment | (B7) E | (B8) V | (B9) E | (B10) V | (B11) E | (B12) V |
| --- | --- | --- | --- | --- | --- | --- | --- |
| DSC: Peak Apex Temp. (° C.) | 143 | 161 | 150 | 159 | 147 | 162 | 151 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodi-

The invention claimed is:

1. A multi-component packaging unit for lightening keratinous fibers, which comprises, formulated separately from one another, a first container comprising a cosmetic agent (A), wherein the agent (A) in the first container with respect to the total weight of the agent (A)—comprises from 4.5% to 12.5% by weight of hydrogen peroxide and a second container comprising a cosmetic agent (B), the agent (B) in the second container consists of levulinic acid and water and has a pH of from 2.2-2.7 and levulinic acid is from 0.7% to 6.5% by weight and a third container comprising a cosmetic agent (C), wherein the agent (C) in the third container comprises (a) at least one persulphate selected from the group consisting of ammonium persulphate, potassium persulphate and sodium persulphate.

2. The multi-component packaging unit as claimed in claim 1, which comprises, formulated separately from one another, a further container comprising a cosmetic agent (D), wherein the agent (D) in this further container comprises (d) at least one alkalizing agent selected from the group consisting of ammonia, 2-aminoethan-1-ol, 2-amino-2-methylpropan-1-ol, 2-amino-2-methylpropan-1,3-diol, L-arginine, D-arginine, D/L-arginine, L-lysine, D-lysine and D/L-lysine.

3. The multi-component packaging unit as claimed in claim 1, wherein the agent (A) in the first container—with respect to the total weight of the agent (A)—comprises from 6.5% to 12.5% by weight of hydrogen peroxide.

* * * * *